US008324276B2

(12) United States Patent
Bryhn

(10) Patent No.: US 8,324,276 B2
(45) Date of Patent: Dec. 4, 2012

(54) FATTY ACID COMPOSITION FOR TREATMENT OF ALZHEIMER'S DISEASE AND COGNITIVE DYSFUNCTION

(75) Inventor: Morten Bryhn, Svelvik (NO)

(73) Assignee: Pronova Biopharma Norge AS (NO)

( * ) Notice: Subject to any disclaimer, the term of this patent is extended or adjusted under 35 U.S.C. 154(b) by 965 days.

(21) Appl. No.: 11/210,115

(22) Filed: Aug. 24, 2005

(65) Prior Publication Data

US 2006/0166935 A1  Jul. 27, 2006

Related U.S. Application Data

(60) Provisional application No. 60/645,604, filed on Jan. 24, 2005.

(30) Foreign Application Priority Data

Jan. 24, 2005  (SE) ...................................... 0500174

(51) Int. Cl.
*A61K 31/20* (2006.01)
(52) U.S. Cl. ...................................... 514/560
(58) Field of Classification Search ................... 514/560
See application file for complete search history.

(56) References Cited

U.S. PATENT DOCUMENTS

| 6,395,778 B1 * | 5/2002 | Luthria ........................ 514/549 |
| 2002/0077361 A1 | 6/2002 | Peet et al. |
| 2003/0032674 A1 * | 2/2003 | Hwang ........................ 514/560 |
| 2003/0077342 A1 | 4/2003 | Maffetone |

FOREIGN PATENT DOCUMENTS

| EP | 0 234 733 | 9/1987 |
| EP | 0 302 481 | 2/1989 |
| EP | 1 157 692 A1 | 11/2001 |
| EP | 1 310 249 A1 | 5/2003 |
| EP | 1 419 780 A1 | 5/2004 |
| FR | 2 761 887 | 10/1998 |
| WO | WO 97/05780 | 2/1997 |
| WO | WO 99/38498 | 8/1999 |
| WO | WO 00/32190 | 6/2000 |
| WO | WO 01/56579 A1 | 2/2001 |
| WO | WO 02/089787 A1 | 11/2002 |
| WO | WO 03/043570 A2 | 5/2003 |
| WO | WO 03/043570 A3 | 5/2003 |
| WO | WO 2004/018598 A1 | 3/2004 |
| WO | WO 2004/047835 A1 | 6/2004 |
| WO | WO 2005/070411 A1 | 8/2005 |
| WO | WO 2006/077495 A1 | 7/2006 |

OTHER PUBLICATIONS

Intelihealth, "Alzheimer's disease," online, accessed Jun. 30, 2008, http://www.intelihealth.com/IH/ihtIH/WSIHW000/8303/9117/195703.html?d=dmtHealthAZ.*
Boston PF, Bennett A, Horrobin DF, and Bennett CN, "Ethyl-EPA in Alzheimer's disease—a pilot study," Prostaglandins Leukotrienes & Essential Fatty Acids, Nov. 2004, 71(5), 341-346.*
Burns A and Zaudig M, "Mild cognitive impairment in older people," The Lancet, Dec. 2002, 360(9349), 1963-1965.*
Ebert U and Kirch W, "Scopolamine model of dementia: electroncephalagram finding and cognitive performance," European Journal of Clinical Investigation, Nov. 1998, 28(11), 944-949.*
Freund-Levi Y, Eriksdotter-Jönhagen M, Cederholm T, Basun H, Faxén-Irving G, Garlind A, Vedin I, Vessby B, Wahlund LO, and Palmblad J, "Omega-3 fatty acid treatment in 174 patients with mild to moderate Alzheimer disease: OmegAD study: a randomized double-blind trial," Archives of Neurology, Oct. 2006, 63(10), 1402-1408.*
Hook VY, "Neuroproteases in Peptide Neurotransmission and Neurodegenerative Diseases," biodrugs, 2006, 20(2), 105-119.*
Holsinger T, Deveau J, Boustani M, and Williams JW Jr, "Does this patient have dementia?", Journal of the American Medical Association, Jun. 2007, 297(21), 2391-2404.*
Jelic V, Kivipelto M, and Winblad B, "Clinical trials in mild congitive impairment: lessons for the future," Journal of Neurology, Neurosurgery and Psychiatry, Apr. 2006, 77(4), 429-438 (Epub Nov. 2005).*
Morris MC, Evans DA, Bienias JL, Tangney CC, Bennett DA, Wilson RR, Aggarwal N, and Schneider J, "Consumption of fish and n-3 fatty acids and risk of incident Alzheimer disease," Archives of Neurology, Jun. 2003, 60(7), 940-946.*
Plourde M, Fortier M, Vandal M, Tremblay-Mercier J, Freemantle E, Bégin M, Pifferi F, and Cunnane SC, "Unresolved issues in the link between docosahexaenoic acid and Alzheimer's disease," Prostaglandins Leukotrienes & Essential Fatty Acids, Nov.-Dec. 2007, 77(5-6), 301-308.*
Standaert DG and Young AB, "Chapter 22, Treatment of Central Nervous System Degenerative Disorders," Goodman & Gilman's The Pharmacological Basis of Therapeutics 10th ed., Hartman JG, Limbird LE, and Gilman AG Eds., McGraw-Hill, New York, 2001, 549-568 (p. 549 and 560-562 provided).*
Rosenberg PB and Lyketsos CG, "Mild cognitive impairment: searching for the prodrome of Alzheimer's disease," World Psychiatry, Jun. 2008, 7(2), 72-78.*
Cognitive Neurology and Alzheimer's Disease Center, "Dementia: Causes, Symptoms, Diagnoses," Northwestern University, http://www.brain.northwestern.edu/ mdad/dementia.html, Dec. 2003 (accessed Jun. 23, 2009).*
MacLean CH, Issa AM, Newberry SJ, Mojica WA, Morton SC, Garland RH, Hilton LG, Traina SB, and Shekelle PG, "Effects of Omega-3 Fatty Acids on Cognitive Function with Aging, Dementia, and Neurological Diseases. Evidence Report/Technology Assessment No. 114," AHRQ Pub. No. 05-E011-2. Rockville, MD, Feb. 2005 (p. i and 15 provided).*
Suzuki H, Morikawa Y, and Takahashi H, "Effect of DHA oil supplementation on intelligence and visual acuity in the elderly," World Review of Nutrition and Dietetics, 2001, 88, 68-71.*
Kyle DJ, Schaefer E, Patton G, and Beiser A, "Low serum docosahexaenoic acid is a significant risk factor for Alzheimer's dementia," Lipids, 1999, 34(Suppl), S245.*

(Continued)

*Primary Examiner* — Paul Zarek
(74) *Attorney, Agent, or Firm* — Finnegan, Henderson, Farabow, Garrett & Dunner, LLP

(57) ABSTRACT

This invention relates to the use of a fatty acid composition comprising at least (all-Z omega-3)-4,7,10,13,16,19-docosahexaenoic acid (DHA), or derivatives thereof, and (all-Z omega-3)-5,8,11,14,17-eicosapentaenoic acid (EPA), or derivatives thereof for manufacturing of a medicinal product or a food stuff for the treatment and/or prevention of amyloidos-related diseases, such as Alzheimer's disease, as well as treatment/prevention of cognitive dysfunction.

26 Claims, 3 Drawing Sheets

OTHER PUBLICATIONS

International-Type Search Report dated Jul. 6, 2005 for Application No. SE 05/00042.
Bhattacharya Ananyo A., et al. Crystallographic Analysis Reveals Common Modes of Binding of Medium and Long-chain Fatty Acids to Human Serum Albumin, (2000), J. Mol. Biol., vol. 303, pp. 721-732.
Donadio, Jr., James V., Use of Fish Oil to Treat Patients With Immunoglobulin A Nephropathy[1-3], (2000), Am J. Clin Nutr, vol. 71 (suppl), pp. 373S-375S.
Hermansen, Leonila F. et al., Purification and Characterization of Amyloid-related Transthyretin Associated With Familial Amyloidotic Cardiomyopathy, (1995), Euro J Biochim, vol. 227, pp. 772-779.
Lim, Giselle P., et al., A Diet Enriched With the Omega-3 Fatty Acid Docosahexaenoic Acid Reduces Amyloid Burden in an Aged Alzheimer Mouse Model, (Mar. 23, 2005), The Journal of Neuroscience, vol. 25, No. 12, pp. 3032-3040.
McIlhinney, R.A. Jeffrey. et al., Studies on the Cellular Location, Physical Properties and Endogenously Attached Lipids of Acylated Proteins in Human Squamous-Carcinoma Cell Lines, (1987), Biochem. J., vol. 244, pp. 109-115.
McLaurin, J., et al., Review: Modulating Factors in Amyloid-β Fibril Formation, (2000), Journal of Structural Biology, vol. 130, pp. 259-270.
Merlini, Giampaolo, MD, et al., Molecular Mechanisms of Amyloidosis, (2003), The New England Journal of Medicine, vol. 349, pp. 583-596.
Miroy, Greta J., et al., Inhibiting Transthyretin Amyloid Fibril Formation Via Protein Stablization, (Dec. 1996), Proc. Natl. Acad. Sci., vol. 95, pp. 15051-15056.
Schmidt, Michael F.G., Fatty Acylation of Proteins, (1989), Biochimica Acta, vol. 988, pp. 411-426.
Westermark, Amyloid Fibril Protein Nomenclature—2002, Amyloid: J. Protein Folding Disord., vol. 9, pp. 197-200.
Wilson, David M., et al., Free Fatty Acids Stimulate the Polymerization of Tau and Amyloid β Peptides, (Jun. 1997), American Journal of Pathology, vol. 150, No. 6, pp. 2181-2195.
Žerovnik, Eva, Amyloid-fibril Formation, (2002), Eur. J. Biochem., vol. 269, pp. 3362-3371.
Andrieu et al., "Nutritional factors in cognitive dysfunction," J. Nutr. Health Aging (2000), vol. 4, p. 194.
Beisiegel et al., "Lipids and lipoproteins in the brain," Arch. Neurol. (2001), vol. 12, pp. 243-244.
Brining et al., "Effects of chronic beta-amyloid treatment on fatty acid incorporation into rat brain," Neurobiol. Aging (1996), vol. 17, pp. 301-309.
Cathcart et al., "A fish oil diet inhibits amyloid P component (AP) acute phase responses in arthritis susceptible mice," J. Immunology (1987), vol. 139, pp. 89-91.
Cathcart et al., "A fish oil diet retards experimental amyloidosis, modulates lymphocyte function, and decreases macrophage arachidonate metabolism in mice," J. Immunology (1987), vol. 139, pp. 1850-1854.
Database WPI: Week 199847, Derwent Publications Ltd., FR 2761887.
File History for EP 04 07 5413.
Freund-Levi et al., "ω-3 fatty acid treatment in 174 patients with mild to moderate Alzheimer Disease: OmegAD Study," Arch. Neurol. (2006), vol. 63, pp. 1402-1408, E1-2.
Freund-Levi et al., "Safety and tolerability of omega-3 fatty acid treatment in patients with Alzheimer's disease," poster presentation, undated.
Gonnerman et al., "Dietary fish oil modulation of macrophage amyloid P component responses in mice," J. Immunology (1988), vol. 140, pp. 796-799.
Kalmijn, "Fatty acid intake and the risk of dementia and cognitive decline: a review of clinical and epidemiological studies," J. Nutr. Health Aging (2000), vol. 4, pp. 202-207.
McCarty, "Vascular nitric oxide, sex hormone replacement, and fish oil may help to prevent Alzheimer's disease by suppressing synthesis of acute-phase cytokines," Med. Hypotheses (1999), vol. 53, pp. 369-374.
Perichon et al., "Peroxisomal disease cell lines with cellular plasmalogen deficiency have impaired muscarinic cholinergic signal transduction activity and amyloid precursor protein secretion," Biochem. Biophys. Res. Commun. (1998), vol. 248, pp. 57-61.
Schaefer et al., "Plasma phosphatidylcholine docosahexaenoic acid content and risk of dementia and Alzheimer Disease," Arch. Neurol. (2006), vol. 63, pp. 1545-1550.
U.S. Appl. No. 60/608,540, filed Sep. 10, 2005, R. Hogg.
Cathcart et al: "Dietary fish oil modulation of macrophage amyloid P component responses in mice" J Immunol Feb. 1, 1988; 140(3):796-9.
Wilson el al: "Free fatty acids stimulate the polymerization of tau and amyloid beta peptides. In vitro evidence for a common effector of pathogenesis in Alzheimer's disease". Am. J. Pathol. (1997), 150(6), 2181-2195.
Freund-Levi et al. "ω-3 Fatty Acid Treatment in 174 Patients with Mild to Moderate Alzheimer Disease: OmegAD Study" Arch Neurol, Oct. 2006; 63; 1402-1408.
Calon et al., "Docosahexaenoic Acid Protects from Dendritic Pathology in an Alzheimer's Disease Mouse Model," 43 Neuron 633-645 (2004).

* cited by examiner

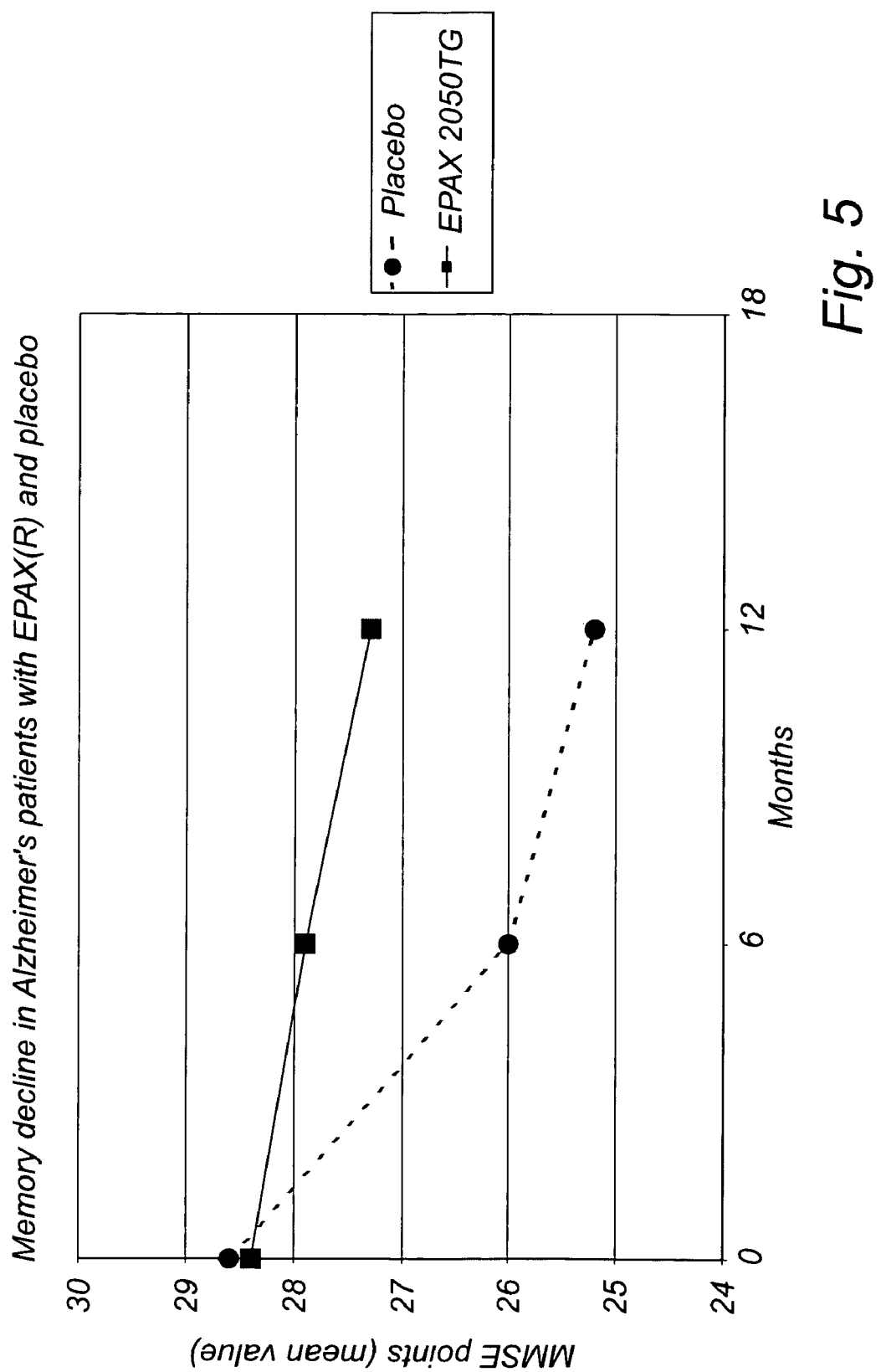

FATTY ACID COMPOSITION FOR TREATMENT OF ALZHEIMER'S DISEASE AND COGNITIVE DYSFUNCTION

This application claims benefit of priority to U.S. Provisional Patent Application No. 60/645,604 filed on Jan. 24, 2005, and Swedish Patent Application No. 0500174-8 filed on Jan. 24, 2005.

TECHNICAL FIELD OF THE INVENTION

The present invention relates to a fatty acid composition for the use in medicinal products as well as in food stuff or food complements for treatment and/or prevention of amyloidos-related diseases, such as Alzheimer's, and/or cognitive dysfunction. Additionally, the present invention relates to methods for treating and/or preventing amyloidos-related diseases, such as Alzheimer's, and/or cognitive dysfunction, which method comprises administering to a patient a therapeutically effective amount of a fatty acid composition.

BACKGROUND ART

The biological function of a protein depends on its three-dimensional structure, which is determined by its amino acid sequence during the process of protein folding. Normal folding is needed for successful cell functioning and therefore important in maintaining health. Several types of diseases have been found where protein misfolding and conformational change are the main causes of appearance and progression of the diseases (1).

Misfolding of proteins may lead to formation of so called fibrils. Proteins or fragment of proteins are converted from their normally soluble forms to insoluble fibrils or plaques, which accumulate in a variety of organs. The final forms of these aggregates often have a well-defined pathological anatomical appearance, known as amyloid.

Despite the range of proteins involved with their unique and characteristic native folds, the fibrils of the amyloid in which they are found in the disease states are extremely similar in their overall appearance. Proteins known to have the propensity of fibrillar conformation in humans, called precursor proteins, are making up a list of 21 exponents (3) and the number is increasing. Usually the protein in the fibril is made up of a small number of amino acids on average around 20-60 grouping them in the category of polypeptides rather than proteins.

Proteins are usually made up of an alfa-helix and a beta-sheet. Amyloid fibrils, however, usually contain beta-sheet material only rendering the molecules physical properties different from the parent protein. While normal proteins are subjected to a continuous process of degradation by proteolysis, one very important feature of fibrils is the ability, once formed, to be essentially indestructible under physiological conditions. The amyloid fibrils are dominated by hydrogen bonding between the amid and the carbonyl groups of the main chain, rather than by specific interactions of the side chains, which determine the structure of normal proteins. This abnormal bonding induced by the large number of hydrogen bonds of the beta-sheet that must be disrupted to rescue the polypeptide chain from the aggregated state, results in a high resistance to degradation and properly removal from the tissue of deposition.

While in alfa-helices the hydrogen bonds are between side groups within the same strand, in beta sheets the bonds are between one strand and another. Since the second beta-strand can come from a different region of the same protein or from a different molecule, formation of beta-sheets is usually stabilised by protein oligomerisation or aggregation. In this manner the misfolded protein self-associates and become deposited in amyloid aggregates in diverse organs, inducing tissue damage and organ dysfunction. An important part of the deposition process is that a critical concentration of the precursor proteins has to be present before fibril formation occurs (4). It also seems that as soon as an amyloid nucleus has been created the process of aggregation and deposition of amyloid material escalates.

Many of the precursor proteins are not directly prone to fibril deformation. However, when peptide fragments of the precursor protein dissociate from the parent molecule such peptides do not have a stable globular fold to protect them against aggregation. Folding of proteins is a function of physical properties inherent from the amino acid sequence of the chain. These so called non-covalent interactions are weak bonding forces, however, the large number of individual contacts within a protein adds up to a large energy factor favouring normal protein folding. The most important force is the hydrophobic interaction but even hydrogen bonds mentioned above are extremely important. Examples of even weaker forces are electrostatic interactions and van der Waals forces. The number of non-covalent interactions is to some degree a function of the protein chain length meaning that splicing of a section of the protein to a peptide will render the peptide with less stability due to the lower number of non-covalent interactions. The normal folding forces will be weaker which could favour the formation of fibrils.

Less known but significantly important for normal folding as well as maintenance of a stable three-dimensional structure, is protein acylation by covalent attachment of fatty acids (5). It is well established that the protein albumin is able to bind several molecules of fatty acids. Saturated fatty acids such as stearic, palmitic and myristic acid are the predominant fatty acids that attach to proteins in eukaryotic cells (6). From studies using radiolabelled fatty acids we know that each fatty acid labels a different sub-population of proteins with the fatty acid interacting with basic amino acids such as lysine, glycine and arginin. The carboxyl group of the fatty acid forms a salt bridge or a hydrogen bond with basic amino acid side chains. All sites have cylindrical hydrophobic channels of varying shape that force the saturated fatty acids to assume a nearly linear configuration. However, the binding pockets are large enough to accommodate unsaturated fatty acids such as oleic acid and arachidonic acid (7).

Interestingly, established amyloid also contains a certain amount of fatty acids. By methanol extraction of amyloid derived from transthyretin about 10% of the dry mass was soluble pointing to the presence of a lipid fraction (8). Gas-chromatography revealed the presence of mixtures of saturated fatty acids like those mentioned above, but also to polyunsaturated fatty acids like palmitoleic acid, linoleic acid, alfa-linolenic acid and arachidonic acid. This pattern of fatty acids is typical for a modern Western diet, which is very much based on saturated fat from dairy products and meat together with seed derived oils. It is quite clear that fatty acids have a function in the normal folding of proteins. The reason why fatty acids are found in amyloid is obscure but interestingly enough the fatty acids found are congruent with the fats of our diet. One hypothesis is based on the assumption that some fatty acids bound to the polypeptide or protein have weaker affinity rendering the chain less stable and therefore prone to fibrillar deformation.

Amyloid deposits can be reabsorbed and organ function reversed if the synthesis of amyloidogenic protein is shut down. There seems to be a fine balance between the rate at which amyloid is formed and its clearance. It may therefore be possible to promote the resorption of amyloid by reducing the concentration of the amyloidogenic protein to a level below a critical threshold without necessarily eliminating the precursor (AA). Studies of the mechanism of conversion from normally soluble precursor proteins into amyloid fibrils have benefited from the fact that the transition can be reproduced under laboratory conditions. In vitro experiments have demonstrated that conversion of native, fully folded protein into a highly amyloidogenic, partially folded conformer could be blocked by stabilizing native proteins with a specific ligand (9). Other experiments using native precursor proteins such as tau-protein (10) and islet amyloid polypeptide (IAPP) (11) have shown a stimulating effect of certain fatty acids on the assembly of fibrils and amyloid. All long-chain fatty acids tested enhanced assembly to some extent, although greater stimulation was associated with unsaturated forms. Both articles concluded that polyunsaturated fatty acids such as arachidonic acid, oleic acid and linoleic acid but also myristic acid exerted pronounced effects on fibril and amyloid formation. It seemed therefore that common unsaturated fatty acids in our diet could stimulate the formation of fibrils and amyloid and consequently increase the risk of inducing disabling diseases like Alzheimer's disease.

SUMMARY OF THE INVENTION

Based on the present invention a number of aspects are presented in the appended claims. These aspects include, but are not limited to:

1. Use of a fatty acid composition for the treatment and/or prevention of amyloidos-related diseases, such as Alzheimer's disease.
2. Use of a fatty acid composition for the treatment and/or prevention of cognitive dysfunction.
3. Use of a food stuff or food supplement comprising a fatty acid composition for the treatment and/or prevention of amyloidos-related diseases, such as Alzheimer's disease.
4. Use of a food stuff or food supplement comprising a fatty acid composition for the treatment and/or prevention of cognitive dysfunction.
5. A method for treatment and/or prevention of amyloidos-related diseases, such as Alzheimer's disease.
6. A method for treatment and/or prevention of cognitive dysfunction.

As used herein, the term "Alzheimer's disease" is to be taken to include both Alzheimer's disease, Alzheimer's dementia and Alzheimer's sclerosis.

A common feature for the above aspects is the use of a fatty acid composition comprising at least a combination of (all-Z omega-3)-4,7,10,13,16,19-docosahexaenoic acid (DHA), or derivatives thereof and (all-Z omega-3)-5,8,11,14,17-eicosapentaenoic acid (EPA), or derivatives thereof.

According to a first aspect of the invention, the invention relates to the use of a fatty acid composition comprising at least a combination of (all-Z omega-3)-4,7,10,13,16,19-docosahexaenoic acid (DHA), or derivatives thereof, and (all-Z omega-3)-5,8,11,14,17-eicosapentaenoic acid (EPA), or derivatives thereof for the production of a medicinal product for the treatment and/or prevention of amyloidos-related diseases, such as Alzheimer's disease.

This first aspect also relates to the use of said fatty acid composition in treatment of amyloidos-related diseases, such as Alzheimer's disease, as well as a medicinal product for treatment of Alzheimers's disease comprising said fatty acid composition.

From research leading to the invention it was surprisingly found that a fatty acid composition according to the invention prevents formation of so called fibrils or plaques, and/or reduces deposed fibrils or plaques, known as amyloid. Moreover, a fatty acid composition according to the invention predominantly containing DHA and EPA, or derivatives thereof, seemed to prevent and/or delay formation of fibrils most effectively, wherein the combination of DHA and EPA may act as an antagonist.

Moreover, the treatment according to the invention could be preventive reducing the propensity of fibril formation as well as therapeutic in situations with established amyloid.

Further, under unfavourable conditions, proteins or fragment of proteins are converted from their normally soluble forms to insoluble fibrils or plaques, which accumulate in a variety of organs including the liver, kidneys, spleen, brain, and internal secretory glands like the beta cells of the pancreas inducing toxic effects on cells and tissue. The final forms of these aggregates often have a well-defined pathological anatomical appearance, known as amyloid. This is the reason for the use of the term amyloidoses to describe many of the clinical conditions with which deposition of amyloid are associated. Thus, as used herein, the term "amyloidos-related" diseases means clinical conditions or diseases with which deposition of amyloid, preferably as a consequence of fibril formation, are associated, such as for instance Alzheimer's disease.

In a second aspect, the present invention relates to the use of a fatty acid composition comprising at least a combination of (all-Z omega-3)-4,7,10,13,16,19-docosahexaenoic acid (DHA), or derivatives thereof, and (all-Z omega-3)-5,8,11,14,17-eicosapentaenoic acid (EPA), or derivatives thereof, for the production of a medicinal product for the treatment and/or prevention of cognitive dysfunction. This second aspect also relates to the use of said fatty acid composition in the treatment of cognitive dysfunction, as well as a medicinal product for treatment of cognitive dysfunction comprising said fatty acid composition.

It was found that the fatty acid composition of the present invention was effective in decreasing the rate of memory decline in patients suffering from cognitive dysfunction, for example in patients suffering from mild cognitive dysfunction.

In a preferred embodiment of both the above first and second aspects of the present invention, the invention relates to the use of a fatty acid composition, wherein the weight ratio of EPA:DHA in the fatty acid composition is 1:2 to 2:1.55.

In another preferred embodiment of both the above first and second aspects of the present invention, the invention relates to the use of a fatty acid composition, wherein the weight ratio of EPA:DHA in the fatty acid composition is 1:X, where X is equal or greater than 1. Please note that X being one of an integer or non-integer.

The term "amount" herein relates to weight or volume of the fatty acid composition.

In addition, the invention also includes a fatty acid composition comprising a combination of one or more DHA and/or EPA derivatives. Moreover, the desired pharmacological and/or therapeutic effect may be achieved by the fatty acid composition according to the invention.

In a preferred embodiment of the invention, EPA and DHA in the fatty acid composition are present in the composition in an EPA:DHA ratio from 1:1 to 1:8. In a more preferred embodiment the EPA:DHA ratio in the fatty acid composition is from about 1:1 to 1:6. In a further embodiment of the invention, the fatty acid composition is a product containing DHA or a DHA-derivative in combination with EPA or an EPA-derivative.

Moreover, in another embodiment, the fatty acids in the composition according to the invention is presented in at least one of esterified form, ethyl ester form, salt form, phospholipid form and free acid form, or any combinations thereof. In a preferred embodiment, the fatty acid composition is comprised of a combination of EPA and DHA in triglyceride form.

In another embodiment, at least DHA is obtained from at least one of vegetable, microbial and animal origins, or combinations thereof. Moreover, in a further embodiment, wherein the fatty acid composition comprising at least a combination of DHA and EPA, at least one of DHA and EPA is obtained from at least one of vegetable, microbial and animal origins or combinations thereof. The medicinal product or pharmaceutical product includes therefore for instance a fatty acid composition comprising at least one of a DHA-containing microbial oil and a mixture of an DHA-containing oil from microbial origin and a EPA-containing oil from a marine origin. Moreover, the fatty acid composition according to the invention may additionally also comprise at least one of arachidonic acid (ARA), docosapentaenoic acid, heneicosapentaenoic acid and octadecatentraenoic or derivatives thereof, or any combinations thereof. Suitably, at least a part of the EPA and/or DHA is produced from a marine oil, preferably a fish oil. Furthermore, in another embodiment of the medicinal product, the fatty acid composition is produced from a marine oil, such as a fish oil.

In a specific embodiment of the invention, the fatty acid composition is comprised of at least a combination of EPA and DHA in triglyceride form. Moreover, it should be pointed out that the fatty acid composition is administered to a human or an animal, preferably orally.

In a specific embodiment of the invention, the medicinal product is in form of a capsule or contained in a sachet. Preferably, the capsule is flavoured. More preferably, the capsule is a gelatine capsule which is flavoured. This embodiment also includes a capsule, therein both the capsules and the encapsulated fatty acid composition are flavoured. By flavouring the capsule as mentioned above, the capsule becomes more attractive to the user. However, a medicinal product according to the invention may also be produced for administration though any other route where the active ingredients may be efficiently absorbed and utilized, e.g. intravenously, subcutaneously, intramuscularly, intranasally, rectally, vaginally or topically.

In another embodiment, said fatty acid composition is administered in an amount providing a daily dosage of 1 g to 15 g of said fatty acid composition for a human. In a preferred embodiment between 2 and 10 g of said fatty acid composition is administered per day, and in a more preferred embodiment between 2 and 8 g of said fatty acid composition. The medicinal product or pharmaceutical composition or pharmaceutical preparation according to the invention may also comprise other substances such as an inert vehicle, or pharmaceutical acceptable adjuvants, carriers, preservatives etc., which are well known in to those skilled in the art. However, the medicinal product may also be administered to an animal, such as a pet or a horse. Moreover, it should be pointed out that the medicinal product may be at least one of an amyloid-preventing agent or amyloid-deposit decreasing agent.

In another embodiment of the invention, the invention relates to a use of a fatty acid composition comprising at least (all-Z omega-3)-4,7,10,13,16,19-docosahexaenoic acid (DHA), or derivatives thereof and (all-Z omega-3)-5,8,11,14,17-eicosapentaenoic acid (EPA), or derivatives thereof, that upon administration to a human or an animal will prevent the formation of aggregates of protein fibrils or plaque and/or reduce deposed fibrils, for the production of a medicinal product for the treatment and/or prevention of amyloidos-related diseases, such as Alzheimer's disease, and/or cognitive dysfunction.

According to a third aspect of the invention, the present invention relates to the use of a fatty acid composition comprising at least (all-Z omega-3)-4,7,10,13,16,19-docosahexaenoic acid (DHA), or derivatives thereof, and (all-Z omega-3)-5,8,11,14,17-eicosapentaenoic acid (EPA), or derivatives thereof, for the production of a food stuff or food supplement for the treatment and/or prevention of amyloidos-related diseases, such as Alzheimer's disease.

From research leading to the invention it was surprisingly found that a fatty acid composition according to the invention prevents formation of so called fibrils or plaques, and/or reduces deposed fibrils or plaques, known as amyloid. A fatty acid composition containing at least a combination of the two fatty acids DHA and EPA seemed to prevent and/or delay formation of fibrils most effectively. Moreover, the use according to above leads to the same advantages and possibilities as mentioned before. The treatment according to the invention could be preventive, reducing the propensity of fibril formation, as well as therapeutic in situations with established amyloid. The definition concerning "amyloidos-related" diseases is also included for the patent positions related to a food stuff or a food supplement according to the invention.

In a fourth aspect, the present invention also provides the use of a fatty acid composition comprising at least (all-Z omega-3)-4,7,10,13,16,19-docosahexaenoic acid (DHA), or derivatives thereof, and (all-Z omega-3)-5,8,11,14,17-eicosapentaenoic acid (EPA), or derivatives thereof, for the production of a food stuff or food supplement for the treatment and/or prevention of cognitive dysfunction.

It was found that the fatty acid composition of the present invention was effective in decreasing the rate of memory decline in patients suffering from cognitive dysfunction, for example in patients suffering from mild cognitive dysfunction.

One advantage of manufacturing and selling a food stuff for the treatment and/or prevention of amyloidos-related diseases, such as Alzheimer's disease, or for treatment and/or prevention of cognitive dysfunction is that such a food stuff will be more easily accessible for people. In preventive purpose they preferably buy the product or supplement in a health store and/or a supermarket, and they do not need to visit a doctor.

In a preferred embodiment of the third and fourth aspects of the present invention, the invention relates to the use of a fatty acid composition, wherein the weight ratio of EPA:DHA in the fatty acid composition is 1:2 to 2:1.55.

In another preferred embodiment of the third and fourth embodiments of the present invention, the invention relates to the use of a fatty acid composition, wherein the weight ratio of EPA:DHA in the fatty acid composition is 1:X, where X is equal or greater than 1. Please note that X being one of an integer or non-integer. In addition, the invention also includes a fatty acid composition comprising at least a combination of one or more DHA and/or EPA derivatives. Moreover, the desired pharmacological and/or therapeutic effect may be achieved by the fatty acid composition according to the invention.

In another embodiment of the invention, EPA and DHA in the fatty acid composition are present in the composition of an EPA:DHA ratio from 1:1 to 1:8. In a more preferred embodiment the EPA:DHA ratio in the fatty acid composition is from about 1:1 to 1:6. In a specific embodiment of the invention, the fatty acid composition is a product of DHA or a DHA-derivative and EPA or an EPA-derivative.

Moreover, in another embodiment, the fatty acids in the composition according to the invention is presented in at least one of esterified form, ethyl ester form, salt form, phospholipid form and free acid form, or any combinations thereof. In a preferred embodiment, the fatty acid composition is comprised of a combination of EPA and DHA in triglyceride form.

Further, in another embodiment, at least DHA is obtained from at least one of vegetable, microbial and animal origins, or combinations thereof. In preferred embodiment, wherein the fatty acid composition comprising at least a combination of DHA and EPA, at least one of DHA and EPA is obtained from at least one of vegetable, microbial and animal origins or combinations thereof. The food stuff or food supplement includes therefore, for instance, a fatty acid composition comprising at least one of a DHA-containing microbial oil and a mixture of an DHA-containing oil from microbial origin and a EPA-containing oil from a marine origin. Further, the fatty acid composition according to the invention may additionally also comprise at least one of arachidonic acid (ARA), docosapentaenoic acid, heneicosapentaenoic acid and octadecatentraenoic or derivatives thereof, or any combinations thereof. Suitably, at least a part of the EPA and/or DHA is produced from a marine oil, preferably a fish oil. Furthermore, in another embodiment of the food stuff or food supplement, the fatty acid composition is produced from a marine oil, such as a fish oil.

In a preferred embodiment of the invention, the fatty acid composition is comprised of at least a combination of EPA and DHA in triglyceride form. Moreover, it should be pointed out that the fatty acid composition is administered to a human or an animal, preferably orally. However, the food stuff or food supplement according to the invention may also be produced for administration though any other route as mentioned before.

In a specific embodiment of the invention, the food stuff or food supplement is in form of a capsule or contained in a sachet. Preferably, the capsule is flavoured. More preferably, the capsule is a gelatine capsule which is flavoured. This embodiment also includes a capsule, therein both the capsules and the encapsulated fatty acid composition are flavoured. By flavouring the capsule as mentioned above, the capsule becomes more attractive to the user.

In another preferred embodiment, said fatty acid composition is administered in an amount providing a daily dosage of 1 g to 15 g of said fatty acid composition for a human. In a more preferred embodiment between 2 and 10 g of said fatty acid composition is administered per day, and in a most preferred embodiment between 2 and 8 g of said fatty acid composition. The food stuff or food supplement according to the invention may also comprise other substances such as an inert vehicle, or pharmaceutical acceptable adjuvants, carriers, preservatives etc., which are well known in to those skilled in the art. Additionally, even the food stuff or food supplement may be administered to an animal such as a pet or a horse. Moreover, it should be pointed out that the food stuff or food supplement may be at least one of an amyloid-preventing agent or amyloid-deposit decreasing agent.

In a specific embodiment, the present invention relates to use of a fatty acid composition comprising at least DHA, or derivatives thereof, and EPA, or derivatives thereof, that upon administration to a human or an animal will prevent the formation of aggregates of protein fibrils or plaque and/or reduce deposed fibrils, for the production of a medicinal product for the treatment and/or prevention of amyloidos-related diseases, such as Alzheimer's disease, and/or cognitive dysfunction. Moreover, one advantage of selling a food stuff for prevention of Alzheimer's disease or a food stuff for preventing cognitive dysfunction is that the food stuff may help people not to develop these diseases in the future.

According to a fifth aspect of the invention, the present invention relates to a method for the treatment and/or prevention of amyloidos-related diseases, such as Alzheimer's disease, wherein an effective amount of a fatty acid composition comprising at least a combination of (all-Z omega-3)-4,7,10,13,16,19-docosahexaenoic acid (DHA), or derivatives thereof, and (all-Z omega-3)-5,8,11,14,17-eicosapentaenoic acid (EPA), or derivatives thereof, is administered to a human or an animal. Herein, "an effective amount" also includes a therapeutically or a pharmaceutically active amount of the fatty acid composition. This expression relates to a dose of said fatty acid composition that will lead to the desired pharmacological and/or therapeutic effect. The desired pharmacological and/or therapeutic effect is, as stated above, achieved by the fatty acid composition according to the invention. From research leading to the invention it was surprisingly found that a fatty acid composition according to the invention prevents formation of so called fibrils or plaques, and/or reduces deposed fibrils or plaques, known as amyloid.

In a sixth aspect, the present invention also relates to a method for the treatment and/or prevention of cognitive dysfunction, wherein an effective amount of a fatty acid composition comprising at least a combination of (all-Z omega-3)-4,7,10,13,16,19-docosahexaenoic acid (DHA), or derivatives thereof, and (all-Z omega-3)-5,8,11,14,17-eicosapentaenoic acid (EPA), or derivatives thereof, is administered to a human or an animal.

It was found that the fatty acid composition of the present invention was effective in decreasing the rate of memory decline in patients suffering from cognitive dysfunction, for example in patients suffering from mild cognitive dysfunction.

In a preferred embodiment of the fifth and sixth aspects of the present invention, the invention relates to the use of a fatty acid composition, wherein the weight ratio of EPA:DHA in the fatty acid composition is 1:2 to 2:1.55. In another preferred embodiment of the fifth and sixth aspect of the invention, the fatty acid composition the weight ratio of EPA:DHA in the fatty acid composition is 1:X, where X is equal or greater than 1. Moreover, the method leads to the same advantages and possibilities as mentioned before.

In a preferred method for treatment of Alzheimer's disease and/or cognitive dysfunction according to the invention, the disease is caused by deposition of amyloid. In a specific embodiment of the invention, the method of treating Alzheimer's disease and/or cognitive dysfunction is related to administering to a human suffering from the disease an effective disease (Alzheimer's and/or cognitive dysfunction) alleviating amount of a amyloid-deposit-decreasing agent. Preferably, the amyloid-deposit-decreasing agent is a fatty acid composition comprising at least one of a combination of the fatty acids DHA, derivatives thereof, and EPA, derivatives thereof.

In another embodiment of the invention, the embodiment relates to use of a fatty acid composition comprising at least a combination of DHA, or derivatives thereof, and EPA, or derivatives thereof, that upon administration to a human or an animal will lead to prevention of, or reduction of, deposition of amyloid, for the manufacture of a medicament or a food supplement, for the treatment and/or prevention of Alzheimer's disease, preferably caused by amyloidosis.

In a specific embodiment of the invention, the fatty acid composition of the present invention, for use in a medical product, food stuff, food supplement or method of treatment comprises at least 70% unsaturated omega-3 fatty acids wherein the fatty acids DHA and EPA are present in a weight ratio from about 1:2 to 2:1.

As used herein, amyloidos-related conditions or diseases, include for example Alzheimer's disease. Such diseases/conditions can be sporadic, inherited or even infectious, and often occur only late in life even if inherited forms may appear much earlier. Each disease is associated with a particular protein and aggregates of these proteins are thought to be the direct origin of the pathological conditions associated with the disease. Moreover, the treatment and/or prevention according to administering the fatty acid composition of the invention may also include at least one of; treatment due to reduction of amyloid aggregates, prevention of misfolding of proteins that may lead to formation of so called fibrils or plaque, treatment due to decreasing of the production of Aβ-protein (amyloid beta protein), and prevention and/or treatment due to inhibiting or slow down the formation of protein fibrils, aggregates, or plaque. Moreover, the present invention also includes prevention of fibril accumulation, or formation, by administering a fatty acid composition according to the invention.

In addition, as used herein the term "treatment" means treatment having a curing or alleviating purpose and the treatment of a amyloidos-related disease, such as Alzheimer's, or cognitive dysfunction can be made either acutely or chronically. By chronically treatment is meant a treatment which continues for weeks or years.

BRIEF DESCRIPTION OF THE DRAWINGS

In the studies and examples below reference is made to the accompanying drawings. Herein, reference is made to the accompanying drawings on which:

FIG. 5 illustrates results from one of the experiments below, showing the effect on the MMSE-scoring by orally administering EPAX® 2050TG to patients suffering from cognitive dysfunction.

DESCRIPTION OF PREFERRED EMBODIMENTS

Figure 1:
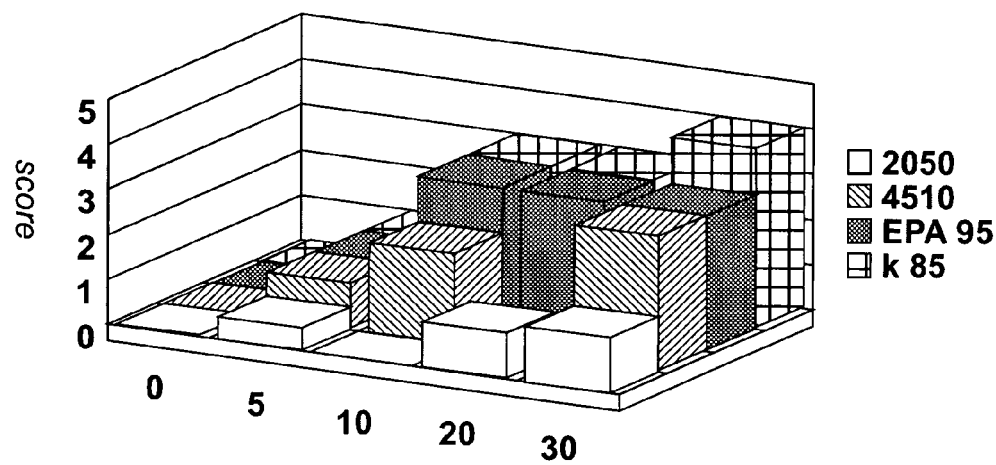
FIG. 1 shows fibril formation of omega-3 preparations during 30 minutes.

A number of preferred embodiments of the invention were performed in order to demonstrate that a fatty acid composition comprising a combination of DHA and EPA is effective on the treatment and/or prevention of amyloidos-related diseases.

Fibril formation is a consequence of misfolding the precursor proteins. The reason for this abnormal behaviour of forming normal three-dimensional structures has not been fully elucidated. As discussed in the background art, it could seem that common polyunsaturated fatty acids frequently recommended by dieticians to prevent cardio-vascular disease and cancer, could in fact increase the propensity of misfolding precursor proteins, thereby inducing amyloid deposition. However, the present invention disclose results showing that another marine long-chain polyunsaturated fatty acid, namely docosahexaenoic acid (DHA), surprisingly seemed to indicating a preventive effect on amyloid formation by prolonging the time to spontaneous fibril formation of IAPP.

The present invention discloses the results of experiments with one synthetic precursor protein, synthetic IAPP, spontaneously forming fibrils. This peptide was incubated with free fatty acids of marine origin comparing the effects on fibril formation with fatty acids like oleic acid and linoleic acid known to stimulate the formation of amyloid fibrils. Moreover, the present invention also discloses results of experiments in a semi-vivo model, where pancreatic islets from transgenic mice producing human IAPP and spontaneously forming beta-call amyloid were prepared and incubated with oleic acid and docosahexaenoic acid.

In a first preferred embodiment, the effects of different omega-3 preparations on fibril formation, were studied.

In a second embodiment, the effects of a fatty acid composition rich in DHA, EPAX 2050® (a high omega-3 oil), an oil comprising at least a combination of DHA and EPA, (K85: approximately 460 mg EPA and 375 mg DHA), and an olive oil, on deposition of amyloid fibrils in pancreatic islets, were studied.

EXAMPLES

In Vitro Experiments on Fibril Formation

In the first study, the effects on fibril formation of different omega-3 preparations were studied. The in vitro fibril formation experiments were performed in small glass test tubes. A stock of dissolved fatty acids in ethanol was prepared by dissolving fatty acids in 100% ethanol at a concentration of 10 mM. After mixing with the same amount of concentrated NaOH, the final concentration of ethanol was 3%. The fatty acids or fatty acid combinations in the table below were tested.

| Fatty acids | Mol. weight | 10 mM contained |
|---|---|---|
| Linoleic acid (from soybean oil) | 278 | 27.8 mg |
| Oleic acid (from olive oil) | 280 | 28.0 mg |
| EPAX DHA concentrate, EPAX2050 (≈500 mg DHA/g and ≈200 mg EPA/g) | 301 | 30.1 mg |
| EPAX 4510 (≈450 mg EPA/g) | 318 | 31.8 mg |
| EPA 95 (≈950 mg EPA/g) | 302 | 30.2 mg |
| K85 (≈465 mg EPA/g and ≈375 mg DHA/g) Control synthIAPP + ethanol | 314 | 31.4 mg |

Figure 2:
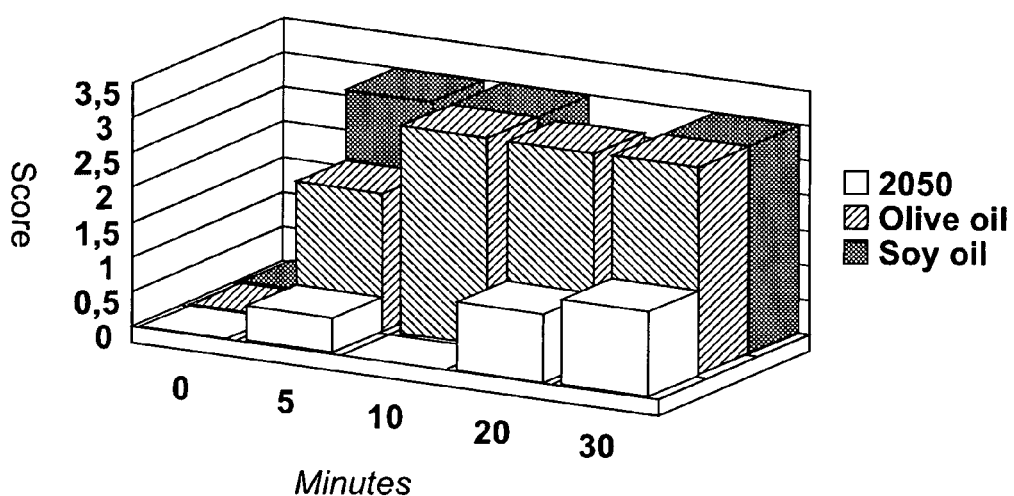
FIG. 2 demonstrates fibril formation between the fatty acid preparations with the most prominent fibril inducing effect, soy oil and olive oil, compared to the fibril preventing DHA-concentrate EPAX 2050 (which comprises approximately 20% EPA and 50% DHA)

Synthetic precursor protein, synthetic IAPP spontaneously forming filbrils, was dissolved in dimethylsulfoxide (DMSO) at a concentration of 10 mg/ml. 25 μM was incubated with each one of the fatty acids, each one in a concentration of 125 μM, in distilled water. One μl aliquots of each sample were analysed after 5, 10, 20, 30, 60, 90, 120, 150, 180, 210, and 240 minutes in the electron microscope after negative contrasting with 2% uranyl acetate in 50% ethanol. Formation of fibrils was observed by electron microscopical analysis and recorded as scores arbitrarily between 0 and 5 in the 30 minutes experiments and between 1 and 2 in the 240 minutes experiments. FIG. 1 demonstrates fibril formation of the omega-3 preparations during 30 minutes. The omega-3 concentrate containing predominantly DHA, EPAX 2050, seemed to prevent or delay the spontaneously formation of fibrils most effectively. Moreover, FIG. 2 demonstrates fibril formation between the fatty acid preparation with the most prominent fibril inducing effect, olive oil and soy oil, compared to the fibril preventing DHA-concentrate EPAX 2050.

Figure 3:
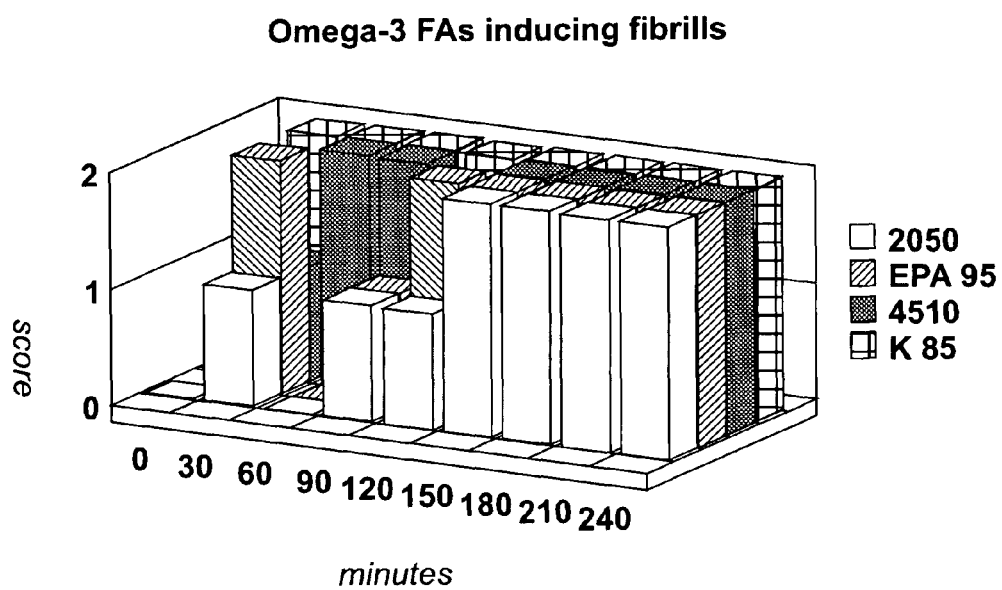
FIG. 3 shows preventive effect against fibril formation up to at least 150 minutes comparing different omega-3 preparations.
Figure 4:
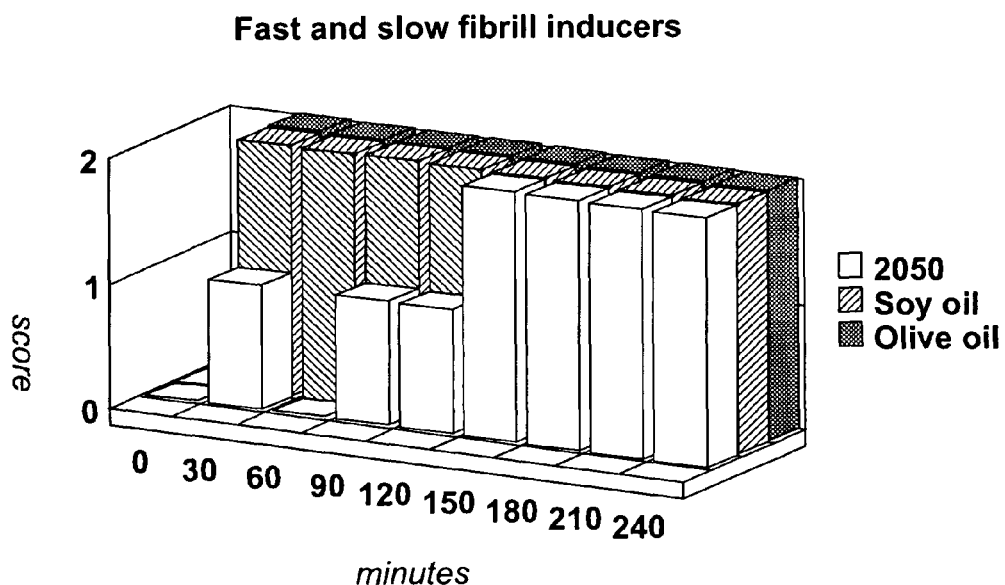
FIG. 4 illustrates effects against fibril formation with a DHA-concentrate compared to olive oil and soy oil.

In addition, fibril induction was also followed for 240 minutes to quantify the fibril preventive effect of the DHA-concentrate. FIG. 3 demonstrates that preventive effect against fibril formation was evident up till 150 minutes in the experiment comparing different omega-3 preparations. Similar prevention was obtained in the experiment with the DHA concentrate compared to olive oil and soy oil, see FIG. 4.

Thus, this study shows that treatment with a fatty acid composition rich in DHA leads to prevention of fibril or plaque formation. Moreover, it seams that DHA act as an fibril inhibitor. At the same time the invention also shows preventive effect on fibril formation of a product comprising at least a combination of DHA and EPA, wherein preferably the amount of DHA≧EPA. The results also suggest a specific preventive effect against fibril formation of an omega-3 product of marine origin comprising EPA and DHA as compared with soy oil and olive oil.

In Vitro Experiments on Amyloid Formation in Pancreatic Islets

In the second study protective effects on amyloid deposition of an olive oil, a high DHA omega-3 oil, and a composition comprising at least DHA and EPA, wherein the amount of EPA≧DHA, were studied.

Transgenic mice carrying the human IAPP gene may be used for studying deposition of amyloid fibrils in the pancreatic islets (11). Therefore, single pancreatic islets were isolated and cultured from transgenic mice. Pancreas were removed under sterile conditions and placed in Hank's balanced salts and finely minced. Small pieces of tissue were enzymatically digested by collagenase for 10 minutes in a 37 degree Celcius water bath. The islets were individually selected under the microscope. Subsequently the islets were cultured overnight in 24 well cell cluster containing RPMI 1640 medium supplemented with 10% fetal bovine serum, penicillin (100 U/ml), streptomycin (1, 1 mg/ml) and 22, 0 mM glucose at 37 degrees in humidified air containing 5% carbonmonoxide.

500 µM of olive oil, high DHA omega-3 oil (EPAX 2050) and K85 oil and 1% fatty acid-free albumin were added to the wells and the islets were cultured in RPMI medium during 2 weeks. There were about 60 islets in each well. Congo red from a stock solution was added to the wells and the islets were examined using light microscopy. Amyloid deposition is stained with Congo red while other cell material does not.

No difference was observed between the different islet groups regarding survival (Table 1).

| Fatty acid | No. of living islets | |
| --- | --- | --- |
| | Start | End |
| EPAX 2050 | 60 | 50 |
| K 85 | 60 | 52 |
| Olive oil | 65 | 54 |

The results of this study shows that 4-5% of the cell islets incubated in the olive oil solution were stained with Congo red indicating intracellular amyloid deposition. Surprisingly only 1% of the cells from islets incubated with high DHA, but even also the K85 concentrate, were stained with Congo red indicating a protective effect against amyloid deposition. However, the DHA rich product, EPAX 2050TG, exhibited stronger effect compared to K85 (EPA≧DHA). Additionally, the results of this study confirm effects supporting prevention and treatment of amyloidos-related diseases influenced of a fatty acid composition comprising at least DHA and EPA, or derivatives thereof.

Prevention of Cognitive Decline

The aim of this study was to evaluate the effects of high dose omega-3 fatty acid supplementation to patients suffering from Alzheimer's disease (AD-patients) in preventing cognitive decline and Alzheimer's disease.

From year 2000 to 2004, 204 AD-patients with a mean age 74±9 (range 54-90) years, under choline esterase inhibitor treatment, were block randomised to either 4 grams daily of omega-3 fatty acids in triglyceride form (~2.8 g DHA and ~1.2 g EPA, EPAX® 2050TG, Pronova Biocare) or placebo (4 g linoleic acid) for 6 months.

After 6 months, all participants received active treatment for 6 more months. Only patients with Mini Mental State Examination (MMSE) >15 points and with no other serious illness were included.

Of the 204 patients participating in the study, 174 patients (73±9 y, 52% women) fulfilled the protocol and are reported here. The drop out rate (n=30) did not differ between the two treatment arms.

Mean MMSE initially in all patients were 23.5±4 points for the group to initially receive treatment and 27±10 points in the group to initially receive placebo.

In the whole group, the decline in cognitive function, i.e MMSE~−0.8±2.6 points, did not differ according to randomisation group at the 6-month follow-up.

However, in the subgroup of patients with mild or very mild cognitive dysfunction, i.e. MMSE >27 points, there was a significant reduction in MMSE decline rate in the treatment group (Δ=−0.5±1.5 points, i.e. from 28.4±0.9 to 27.9±1.9 points, n=19) over the first 6 month treatment period in comparison with the placebo group (Δ=−2.6±2.8 points, i.e. from 28.6±1.1 to 26±2.1 points, n=12) (p<0.05 between groups).

A similar arrest in decline rate was observed in the placebo group (MMSE >27 p) when they received active omega-3 fatty acid treatment between 6 and 12 months (from 26±2.1 to 25.2±3.1 p). The results for the patient subgroup having initial MMSE >27 is shown in FIG. 5.

These results indicates that high doses of a combination of the omega-3 fatty acids DHA and EPA, given to patients with mild or very mild cognitive dysfunction and/or mild or very mild Alzheimer's disease, delayed the rate of cognitive decline according to MMSE.

Discussion

In the studies presented above, the synthetic precursor protein IAPP spontaneously forming fibrils were incubated in vitro with a series of fatty acids of the omega-3 series as well as omega-6 and omega-9. The omega-3 concentrate containing DHA and EPA seemed to prevent or delay the spontaneous formation of fibrils while the omega-6 (soybean oil) and omega-9 (olive oil) fatty acids seemed to provoke fibril formation. The last pattern is known from previous experiments (10, 11). The preventive effect of the combination of DHA and EPA, however, is an unexpected finding. Other omega-3 fatty acids did not have the same effect as DHA:EPA even if some preventive effects were observed compared to the omega-6 and 9 oils. Moreover, in the amyloid in vitro model on islets from transgenic IAPP producing mice DHA, but even another high omega-concentrate, K85, induced amyloid deposition to a significant less extent compared to the omega-9 olive oil.

The present findings indicate a novel therapeutic modality to diseases caused by amyloid deposition. The treatment could be preventive reducing the propensity of fibril formation as well as therapeutic in situations with established amyloid.

Finally, the results support the use of a medicinal product, a pharmaceutical composition, a food stuff or a food supplement, comprising a fatty acid composition comprising a combination of DHA and EPA, for the treatment and/or prevention of amyloidos-related diseases, such as for instance Alzheimer's disease, as well as for cognitive dysfunction.

The invention shall not be limited to the shown embodiments and examples.

REFERENCES

1) Zerovnik A. Eur J Biochem 2002; 269:3362-3371
2) Merlini G and Belotti V. NEJM 2003; 349:583-596
3) Westermark P, Benson M D, Buxbaum J N, et al. Amyloid 2002; 9:197-200
4) McLaurin J, Yang D, Yip C M, et al. J Struct Biol 2000; 130:259-270
5) Schmidt M F G. Biochim. Biophys. Acta 1989; 988:411-426
6) Mclhinney R A J, Cdadwixk J K, and Pelly S J. Biochim. 1987; 244:109-115
7) Bhattacharya A A. J Mol Biol 2000; 303:721-732
8) Hermansen L F, Bergman T, Jörnvall H, et al. Eur J Biochim 1995; 227:772-779
9) Miroy G J, Lai Z, Lashuel H A, et al. Proc Natl Acad Sci USA 1996; 93:15051-15056
10) Wilson D M and Binder L I. Am J Pathol 1997; 150:2181-2195)
11) Ma Z and Westermark G T. Medical Dissertation No. 655, Linkoping, Sweden 2001

The invention claimed is:

1. A method for alleviating an amyloidosis related disease in a subject in need thereof, wherein said disease is Alzheimer's disease, comprising administering to the subject a therapeutically effective amount of a fatty acid composition comprising (all-Z omega-3)-4,7,10,13,16,19-docosahexaenoic acid (DHA) and (all-Z omega-3)-5,8,11,14,17-eicosapentaenoic acid (EPA), with a daily dosage of the composition ranging from 2 g to 10 g, wherein said composition is chosen from a medicinal product and a food supplement, wherein the composition comprises at least 70% unsaturated omega-3 fatty acids.

2. A method for alleviating cognitive dysfunction in a subject in need thereof comprising administering to the subject a therapeutically effective amount of a fatty acid composition comprising (all-Z omega-3)-4,7,10,13,16,19-docosahexaenoic acid (DHA), and (all-Z omega-3)-5,8,11,14,17-eicosapentaenoic acid (EPA), with a daily dosage of the composition ranging from 2 g to 10 g, wherein said composition is chosen from a medicinal product and a food supplement, wherein the composition comprises at least 70% unsaturated omega-3 fatty acids.

3. The method according to claim 1, wherein EPA and DHA are present in the composition in an EPA:DHA ratio ranging from about 1:2 to 2:1.55.

4. The method according to claim 1, wherein the weight ratio of EPA:DHA in the fatty acid composition is 1:X, where X is equal or greater than 1.

5. The method according to claim 4, wherein EPA and DHA are present in the composition in an EPA:DHA ratio ranging from 1:1 to 1:8.

6. The method according to claim 1, wherein the fatty acids in the composition are present in at least one form chosen from esterified form, ethyl ester form, salt form, free acid form, and phospholipid form, or any combinations thereof.

7. The method according to claim 1, wherein DHA is obtained from at least one of vegetable, microbial, and animal origins, or combinations thereof.

8. The method according to claim 1, wherein the DHA, EPA, or both are obtained from at least one of vegetable, microbial, and animal origins, or combinations thereof.

9. The method according to claim 1, wherein the EPA, DHA, or both are produced from a marine oil.

10. The method according to claim 1, wherein the fatty acid composition is produced from a marine oil.

11. The method according to claim 1, wherein the fatty acid composition comprises a combination of EPA and DHA in triglyceride form.

12. The method according to claim 1, wherein the fatty acid composition is administered orally to a human or an animal.

13. The method according to claim 1, wherein the fatty acid composition is chosen from an amyloid-preventing agent and an amyloid-decreasing agent.

14. The method according to claim 2, wherein said cognitive dysfunction is a mild cognitive dysfunction.

15. The method according to claim 1, wherein said fatty acid composition is in an oral dosage form chosen from a capsule and a sachet.

16. The method according to claim 15, wherein said oral dosage form is flavoured.

17. The method according to claim 5, wherein the combination of EPA and DHA is present in the composition in an EPA:DHA ratio ranging from 1:1 to 1:6.

18. The method according to claim 9, wherein at least a part of the EPA, DHA, or both is produced from a fish oil.

19. The method according to claim 1, wherein said fatty acid composition is administered in an amount providing a daily dosage ranging from 2 to 6 g in a human.

20. A method for delaying cognitive decline in a subject in need thereof comprising administering to the subject a therapeutically effective amount of a fatty acid composition comprising (all-Z omega-3)-4,7,10,13,16,19-docosahexaenoic acid (DHA), and (all-Z omega-3)-5,8,11,14,17-eicosapentaenoic acid (EPA), wherein said fatty acid composition is chosen from a medicinal product and a food supplement, wherein the composition comprises at least 70% unsaturated omega-3 fatty acids.

21. The method according to claim 20, wherein the fatty acids in the composition are present in at least one form chosen from esterified form, ethyl ester form, salt form, free acid form, and phospholipid form, or any combinations thereof.

22. The method according to claim 20, wherein at least one of DHA and EPA is obtained from a marine oil.

23. The method according to claim 20, wherein EPA and DHA are present in the composition in an EPA:DMA ratio ranging from 1:1 to 1:8.

24. The method according to claim 20, wherein the fatty acid composition comprises a combination of EPA and DHA in triglyceride form.

25. The method according to claim 20, wherein said fatty acid composition is a food supplement.

26. The method according to claim 20, wherein said fatty acid composition is administered in an amount providing a daily dosage ranging from 1 to 15 g in a human.

* * * * *

UNITED STATES PATENT AND TRADEMARK OFFICE
CERTIFICATE OF CORRECTION

| | | |
|---|---|---|
| PATENT NO. | : 8,324,276 B2 | Page 1 of 1 |
| APPLICATION NO. | : 11/210115 | |
| DATED | : December 4, 2012 | |
| INVENTOR(S) | : Bryhn | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,159 days.

Signed and Sealed this
Eleventh Day of November, 2014

Michelle K. Lee
*Deputy Director of the United States Patent and Trademark Office*